United States Patent
Kulkarni et al.

(10) Patent No.: US 6,316,615 B1
(45) Date of Patent: Nov. 13, 2001

(54) PROCESS FOR THE RECOVERY OF POTASSIUM BITARTRATE AND OTHER PRODUCTS FROM TAMARIND PULP

(75) Inventors: Mohan Gopalkrishna Kulkarni; Madhav Jagannath Thakar; Sudhir Sharadchandra Kulkarni; Sanjay Narayan Nene; Bhaskar Ganapatrao Gaikwad, all of Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/323,478

(22) Filed: Jun. 1, 1999

Related U.S. Application Data

(63) Continuation-in-part of application No. 08/907,891, filed on Aug. 11, 1997, now Pat. No. 5,994,533.

(30) Foreign Application Priority Data

Jun. 24, 1997 (IN) .............................................. 1763/Del/97
Nov. 27, 1998 (IN) .............................................. 3562/Del/98

(51) Int. Cl.[7] ........................................................ C07H 1/08
(52) U.S. Cl. ........................ 536/128; 536/124; 536/127; 536/114; 424/195.1
(58) Field of Search .................................. 536/114, 124, 536/127, 128; 424/195.1

(56) References Cited

U.S. PATENT DOCUMENTS 5,994,533 * 11/1999 Kulkarni et al. .

* cited by examiner

*Primary Examiner*—James O. Wilson
(74) *Attorney, Agent, or Firm*—Birch, Stewart, Kolasch & Birch, LLP

(57) ABSTRACT

The invention relates to a novel process for the recovery of potassium bitartrate and pectin, sugars, fruit acids as by-products from tamarind pulp.

11 Claims, No Drawings

PROCESS FOR THE RECOVERY OF POTASSIUM BITARTRATE AND OTHER PRODUCTS FROM TAMARIND PULP

This application is a continuation-in-part of application Ser. No. 08/907,891 filed on Aug. 11, 1997, now U.S. Pat. No. 5,994,533 entire contents of which are hereby incorporated by reference.

FIELD OF THE INVENTION

This invention relates to a new process for the recovery of potassium bitartarate and other by-products such as pectin, sugars, fruit acids from tamarind pulp. More particularly, it relates to the recovery of potassium bitartarate, pectin, fruit sugar, and other fruit acids from tamarind pulp.

BACKGROUND

Tamarind (*tamarindus indica*) is a widely grown tree found in the tropical countries, the fruits of which contain as much as 10–15% of L(+) tartaric acid depending on the source of origin and the stage of muturation of the fruit. It therefore is a potential source for the recovery of tartaric acid. Efforts to recover tartaric acid from tamarind pulp in the past were based on the treatment of pulp extract with calcium hydroxide and subsequent acidification of calcium tartarate which generated tartaric acid and calcium sulfate. These methods suffered from the drawback that pectin also gets precipitated in the form of calcium pectate along with calcium tartarate which was extremely difficult to separate from calcium tartarate. Alternatively, L(+) tartaric acid was recovered from the tamarind pulp by aqueous extraction followed by treatment with ion exchange resins. Ion exchange methods adopted in the past suffered from the limitation that rapid fouling of the columns occurred making the recovery of the tartaric acid economically unattractive. This was because other ingredients present in the tamarind pulp which can foul the column were not removed prior to the ion exchange treatment.

In the our co-pending Indian Patent Application No.857/Del/96 (not published) filed by the applicants a process for the recovery of tartaric acid, potassium bitartarate, pectin, and fruit sugar from tamarind pulp has been described. The process enables the recovery of four products of commercial value from tamarind pulp, not hitherto commercially exploited for the recovery of potassium bitartarate, tartaric acid, pectin and fruit sugar. Hence, the said process is economically more competitive that other conventional processes employing wine argols for the recovery of potassium bitartarate, tartaric and pectin and sugar. The process is devised such that the recovery of each of the subsequent products is simplified to a great extent. Each product is recovered in high purity so as to meet the specification of the food and pharmaceutical industry. However, the disadvantage of this process is that the tartaric acid is first recovered as calcium tartarate which is subsequently acidified. This yields tartaric acid along with calcium sulphate as a by-product posing waste disposal problems. On the other hand, the process of the present invention does not pose any such problems. The process of the present invention is environment friendly, economical and simple.

Another co-pending U.S. patent application Ser. No. 08/907,891 filed by the Applicants also relates to a process for the recovery of tartaric acid from tamarind pulp. In the process described in this application, tamarind pulp was extracted in water. The aqueous solution was decolorized. It was concentrated and potassium tartarate was separated and recovered as a residue. The aqueous solution was then treated with an organic solvent to precipitate pectin, which was separated and purified. The organic solvent was then evaporated and the remaining aqueous solution was diluted and extracted into an organic layer, recovered the aqueous layer by adding the water and raising temperature to 50° C.–80° C. This aqueous solution was then concentrated and tartaric acid recovered by crystallization. The aqueous raffinate from solvent extracts was passed over ion exchange resin and concentrated to obtain fruit sugars. The present patent application describes an improved process for recovery of potassium bitartarate, pectin, sugars and tartaric acid from tamarind pulp wherein the steps of recovery of value added products from tamarind pulp is simplified. The process becomes economically more attractive. The process of recovery of value added products eliminates the efforts involved in self extraction in organic layer, transfer, aqueous layer, recovery of their organic layer and solvent recovery step.

It is now observed that all above-mentioned stages can be eliminated by using a simple process which is more economical and viable. The said process can also be performed easily without costly apparatus.

OBJECTS OF THE INVENTION

The main objective of the present invention is to provide a novel and simple process for the recovery of potassium bitartarate and simultaneously recover pectin, sugars and other fruit acids as valuable by-products of commercial importance.

DETAILED DESCRIPTION OF THE INVENTION

Accordingly the present invention provides a new process for the recovery of potassium bitartarate and other products such as pectin, sugars, fruit acids as by-products from tamarind pulp which comprises (i) extracting Tamarind pulp in 1–8 steps using 1:1 to 1:8 volumes of water, at a temperature in the range of 25 to 100° C., in a conventional manner for about 0.5–6 hrs, to extract the mixture of tartaric acid, potassium bitartarate, pectin, sugar and other fruit acids in aqueous medium in quantitative manner, (ii) separating the residue and the supernatant liquid by conventional methods, treating the supernatant with a conventional decolourising agent for a period of 0.5 to 2 hrs., separting the decolourising agent by conventional methods, to obtain clear liquid, concentration the liquid separated, to reduce the volume of ½ to ¹⁄₁₀th of the original volume, at a temperature in the range of 60° C. to 90° C. under vacuum ranging between 20 mm to 80 mm to get a pulp, cooling the said concentrated pulp to 5 to 30° C. allowing it to stand for 2–16 hrs, to bring about complete separation of potassium bitartarate, and recovering from mother liquor potassium bitartarate by conventional methods.

(iii) treating the mother liquor obtained in step (ii) containing small amount of potassium bitartarate, pectin, tartaric acid, sugar and the fruit acids with an organic solvent capable of precipitating pectin, washing the precipitate so formed by gradient washing with solvent; water mixture, further purifying pectin by treating it with acidified solvent:water mixture, (iv) removing the solvent from filtrate containing solvent, tartaric acid, traces of potassium bitartarate, sugar and other fruit acids, obtained in step (iii) completely, treating further the aqueous extract free from solvent with decolourising agent for a period ranging between 0.25 to 2 hrs, separating the decolourising agent by conventional methods, concentrating, and cooling to a temperature in the range 30 to 5° C., further treating it with dilute aqueous alkali hydroxide solution for precipitation of additional potassium bitartarate, separating the supernatant and precipitate of potassium bitartarate by known methods, passing the said supernatant from step (iv) rich in sugar, other fruit acids and containing small amount of potassium bitartarate over a conventional strong anion exchange resin to retain acids over the resin to separate sugar syrup which is concentrated to 60–70% sugar content, separating the sugar from the syrup by conventional methods if so desired, and eluting the fruit acid adsorbed on the resin column by either a mineral acid or an alkali, recrystalizing to obtain the fruit acids if so desired, (v) pooling the precipitate of potassium bi-tartarate obtained in step (ii) and (iv) and purifying by known crystallization methods.

In one of the embodiments of the present invention the solvent used in solvent:water mixture for precipitation of pectin is selected from a family of alcohols exemplified by methanol, ethanol, propanol, isopropanol, or ketones like acetone, methyl ethyl ketone, methyl isobutyl ketone or mixture of these solvents with water.

In yet another embodiment the acid used to acidify the solvent:water mixture may be a mineral acid exemplified by hydrochloric acid, sulphuric acid, nitric acid preferably hydrochloric acid.

In yet another embodiment of the present invention the ion exchange resin could be chosen from a family of either gel type or macroporous strong, weak or medium basic anion exchange resin having exchange capacity in the range 0.2–3, preferably 0.5–2.5 and most preferably 1–2 meq/ml.

In yet another embodiment of the present invention the decolourising agent may be selected from activated carbon, fuller's earth, kiesselguhr, preferably activated carbon.

The process of the present invention is described herein below with reference to following examples which are illustrative only and should not be construed to limit the scope of the present invention in any manner.

Example 1

500 gms of tamarind pulp was extracted for one hr with 2 ltrs water, preheated to 75° C., another 2 ltrs of water at 70° C. was added and extraction continued for another hour. The suspension was filtered and the filtrate was mixed with 40 gms activated charcoal, stirred for 15 min at 70° C. and filtered to remove activated charcoal. The filtrate was centrifuged to obtain a clear solution. This was vacuum concentrated at 50° C. to reduce the volume to 400 ml. The concentrate was then cooled to 10° C. and allowed to stand for 4 hrs. The salt precipitated was recovered by filtration. The salt was washed with 2 aliquots of 50 ml of water at 5° C. and washings added to the filtrate. The salt was recrystalized from hot water at 70° C. to yield 18 gm of potassium bitartarate, having purity >99%.

The filtrate obtained after removal of potassium bitartarate was mixed with one ltr of methanol and stirred for 30 min. The pectin precipitated was washed with 100 ml 70:30 methanol:water mixture and then with 100 ml 75:25 methanol:water mixture and finally with 50 ml methanol and then dried at 60° C. under vacuum to obtain dry pectin (yield 20 gm), Pectin was further purified by washing it with acidified methanol:water mixture, followed by washing with methanol:water mixture to remove excess acid and then drying.

The filtrate obtained after recovery of pectin was vacuum concentrated to recover methanol completely, and the filtrate was mixed with 10 g, activated charcoal, stirred for 15 min at 75° C. and filtered to remove activated charcoal. The carbon treatment was repeated. The filtrate was then vacuum concentrated at 60° C. to reduce the volume to 700 ml. The concentrate was then cooled to 10° C. and then 125 ml 20% aqueous potassium hydroxide solution added to it.

The salt precipitated was recovered by filtration. The salt was washed with 2 aliquots of 50 ml water at 5° C. and washings added to the filtrate. The salt was recrystalized from hot water at 75° C. to yield 40 g potassium bitartarate having purity >99%.

The aqueous sugar solution containing other fruit acids was passed over a strong anion exchange macroporous resin at OH form having an exchange capacity 2 meq/ml. The solution was vacuum concentrated at 60° C. till the sugar content was 65%.

The other fruit acids on resin column were recovered by passing 1 N hydrochloric acid through the column. This aqueous acid solution was concentrated and recrystalized to yield recrystalized fruit acids. The yield of fruit acids was 8 g.

Alternatively the fruit acids on the resin column can also be recovered as their potassium salts by passing 1N KOH through the column.

Example 2

500 gms of tamarind pulp was extracted is six steps with 1 ltrs water at 30° C., for half an hour each. The extracts were collected, mixed and filtered. The filtrate was mixed with 80 gms activated charcoal, stirred for 30 min. at 75° C. and filtered to remove activated charcoal. The filtrate was centrifuged to obtain a clear solution. This was vacuum concentrated at 60° C. to reduce the volume to 375 ml. The concentrate was then cooled to 5° C. and allowed to stand for 6 hrs. The salt precipitated was recovered by filtration. The salt was washed with 3 aliquots of 50 ml of water at 5° C. and washings added to the filtrate. The salt was recrystalized from hot water at 70° C. to yield 19 gm of potassium bitartarate, having purity >99%.

The filtrate obtained after removal of potassium bitartarate was mixed with two ltrs of ethanol and stirred for 45 min. The pectin precipitated was filtered and then washed with 75 ml 50:50 ethanol:water mixture and finally with 75 ml ethanol and then dried at 65° C. under vacuum to obtain dry pectin (Yield 15 g). It was further purified by washing it with acidified ethanol:water mixture followed by washing with ethanol:water mixture to remove excess acid and then drying.

The filtrate obtained after recovery of pectin was vacuum concentrated to recover ethanol completely, and the filtrate was mixed 5 g activated charcoal, stirred for 30 min at 60° C. and filtered to remove activated charcoal. The carbon treatment was repeated. The filtrate was then vacuum concentrated at 65° C. to reduce the volume to 500 ml. The concentrate was then cooled to 15° C. and then 100 ml 20% aqueous potassium hydroxide solution added to it. The salt precipitated was recovered by filtration. The salt was washed with 3 aliquots of 50 ml water at 10° C. and washing added to the filtrate. The salt was recrystalized from hot water at 80° C. to yield 37 g, potassium bitartarate having purity >99%.

The aqueous sugar solution containing other fruit acids was passed over a strong anion exchange macroporous resin in OH form having an exchange capacity 1 meq/ml. The solution was vacuum concentrated at 60° C. till the sugar content was 65%.

The other fruit acids on resin column were recovered by passing 1N hydrochloric acid through the column. This aqueous acid solution was concentrated and recrystalized to yield fruit acids. The yield of fruit acids was 7 g.

Alternatively the fruit acids on the resin column can also be recovered as their potassium salts by passing 1N KOH through the column.

500 gms of tamarind pulp was extracted for 1 hr. with 1.5 hrs water, preheated to 80° C. and the extraction was continued for another half an hour. The suspension was filtered. The filtrate was mixed with 35 gms, activated charcoal, stirred for 20 min. at 45° C. and filtered to remove activated charcoal. The filtrate was centrifuged to obtain a clear solution. This was vacuum concentrated at 60° C. to reduce the volume to 350 ml. The concentrate was then cooled to 5° C. and allowed to stand for 10 hrs. The salt precipitated was recovered by filtration. The salt was washed with 4 aliquots of 50 ml of water at 10° C. and washings added to the filtrate. The salt was recrystalized from hot water at 75° C. to yield 20 gm of potassium bitartarate, having purity >99%.

The filtrate obtained after removal of potassium bitartarate was mixed with 1.5 ltrs of isopropanol and stirred for 1 hr. The pectin precipitated was filtered and then washed with 400 ml 80:20 isopropanol:water mixture and then with 400 ml 90:10 isopropanol:water mixture and finally with 400 ml isopropanol and then dried at 60° C. under vacuum to obtain dry pectin (yield 14 g). Pectin was further purified by washing it with acidified isopropanol:water mixture followed by washing with isopropanol:water mixture to remove excess acid and then drying.

The filtrate obtained after recovery of pectin was vacuum concentrated to recover isopropanol completely, and the filtrate was mixed with 15 g activated charcoal, stirred for 15 min at 80° C. and filtered to remove activated charcoal. The carbon treatment was repeated. The filtrate was then vacuum concentrated at 70° C. to reduce the volume to 350 ml. The concentrate was then cooled to 10° C. and then 180 ml 20% aqueous potassium hydroxide solution added to it. The salt precipitated was recovered by filtration. The salt was washed with 5 aliquots of 50 ml water at 15° C. and washings added to the filtrate. The salt was recrystalized from hot water at 85° C. to yield 55 g, potassium bitartarate having purity >99%.

The aqueous sugar solution containing other fruit acids was passed over a strong anion exchange macroporous resin in OH form having an exchange capacity 2 meq/ml. The solution was vacuum concentrated at 65° C. till the sugar content was 65%.

The other fruit acids on resin column were recovered by passing 1N hydrochloric acid through the column. This aqueous acid solution was concentrated and recrystalized to yield recrystalized fruit acids. The yield of fruit acids was 10 g.

Alternatively the fruit acids on the resin column can also be recovered as their potassium salts by passing 1 N KOH through the column.

Example 4

500 gms of tamarind pulp was extracted for one hr with 2 ltrs water, preheated to 75° C., another 1.5 ltrs. of water at 75° C. was added and the extraction continued for another half an hour. The filtrate was mixed with 25 gms activated charcoal, stirred for 15 min. at 65° C. and filtered to remove activated charcoal. The filtrate was centrifuged to obtain a clear solution. This was vacuum concentrated at 50° C. to reduce the volume to 500 ml. The concentrate was then cooled to 10° C. and allowed to stand for 2 hrs. The salt precipitated was recovered by filtration. The salt was washed with 2 aliquots of 50 ml of water at 15° C. and washings added to the filtrate. The salt was recrystalized from hot water at 80° C. to yield 17 gm of potassium bitartarate, having purity >99%.

The filtrate obtained after removal of potassium bitartarate was mixed with two ltrs of acetone and stirred for 20 min. The pectin precipitated was filtered and then washed first with 200 ml 75:25 acetone:water mixture, then with 150 ml 85 15 acetone:water mixture and finally with 100 ml acetone and then dried at 60° C. under vacuum to obtain dry pectin (yield 18 g). Pectin was further purified by washing it with acidified acetone:water mixture followed by washing with acetone:water mixture to remove excess acid and then drying.

The filtrate obtained after recovery of pectin was vacuum concentrated to recover acetone completely, and the filtrate was mixed with 20 g activated charcoal, stirred for 15 min at 85° C. and filtered to remove activated charcoal. The carbon treatment was repeated. The filtrate was then vacuum concentrated at 55° C. to reduce the volume to 450 ml. The concentrate was then cooled to 7° C. and then 150 ml 20% aqueous potassium hydroxide solution added to it. The salt precipitated was recovered by filtration. The salt was washed with 4 aliquots of 50 ml water at 10° C. and washings added to the filtrate. The salt was recrystalized from hot water at 70° C. to yield 50 g potassium bitartarate having purity >99%.

The aqueous sugar solution containing other fruit acids was passed over a strong anion exchange macroporous resin in OH form having an exchange capacity 2 meq/ml. The solution was vacuum concentrated at 70° C. till the sugar content was 65%.

The other fruit on resin column were recovered by passed 1N hydrochloric acid through the column. This aqueous acid solution was concentrated and recrystalized to yield recrystalized fruit acids. The yield of fruit acids was 8 g.

Alternatively the fruit acids on the resin column can also be recovered as their potassium salts by passing 1N KOH through the column.

Example 5

500 gms tamarind pulp was extracted for one hr with 2 ltrs water, preheated to 60° C., another 2 ltrs of water at 60° C. was added and the extraction continued for another two hours. The suspension was filtered. The filtrate was mixed with 40 gms activated charcoal, stirred for 15 min. at 55° C. and filtered to remove activated charcoal. The filtrate was centrifuged to obtain a clear solution. This was vacuum concentrated at 65° C. to reduce the volume to 550 ml. The concentrate was then cooled to 10° C. and allowed to stand for 1 hr. The salt precipitated was recovered by filtration. The salt was washed with 5 aliquots of 50 ml of water at 10° C. and washings added to the filtrate. The salt was recrystalized from hot water at 70° C. to yield 18 gm of potassium bitartarate, having purity >99%.

The filtrate obtained removal of potassium bitartarate was mixed with 1.5 ltrs of 85:15 methanol:water mixture and stirred for 40 min. The pectin precipitated was filtered and then washed first with 150 ml 50:50 methanol:water mixture, then with 150 ml 90:10 methanol:water and finally with 200 ml methanol and then dried at 75° C. under vacuum to obtain dry pectin (yield 13 g). Pectin was further purified by washing it with acidified methanol:water mixture followed by washing with methanol:water mixture to remove excess acid and then drying.

The filtrate obtained after recovery of pectin was vacuum concentrated to recover methanol completely, and the filtrate was mixed with 12 g activated charcoal, stirred for 20 min at 55° C. and filtered to remove activated charcoal. The carbon treatment was repeated. The filtrate was then vacuum concentrated at 50° C. to reduce the volume to 600 ml. The concentrate was then cooled to 10° C. and then 85 ml 20% aqueous potassium hydroxide solution added to it. The salt precipitated was recovered by filtration. The salt was washed with 3 aliquots of 50 ml water at 15° C. and washings added to the filtrate. The salt was recrystalized from hot water 80° C. to yield 35 g potassium bitartarate having purity >99%.

The aqueous sugar solution containing other fruit acids was passed over a strong anion exchange macroporous resin in OH form having an exchange capacity 1 meq/ml. The solution was vacuum concentrated at 65° C. till the sugar content was 65%.

The other fruit acids on resin column were recovered by passing 1N hydrochloric acid through the column. This aqueous acid solution was concentrated and recrystalized to yield recrystalized fruit acids. The yield of fruit acids was 9 g.

Alternatively the fruit acids on the resin column can also be recovered as their potassium salts by passing in 1N KOH through the column.

Example 6

500 gms of tamarind pulp was extracted for one hr with 2 ltrs water, preheated to 75° C., another 3 ltrs of water at 70° C. was added and the extraction continued for another hour. The filtrate was mixed with 20 gms activated charcoal stirred for 30 min at 80° C. and filtered to remove activated charcoal. The filtrate was centrifuged to obtain a clear solution. This was vacuum concentrated at 70° C. to reduce the volume to 600 ml. The concentrate was then cooled to 10° C. and allowed to stand for 1.5 hrs. The salt precipitated was recovered by filtration. The salt was washed with 2 aliquots of 50 of water at 5° C. and washings added to the filtrate. The salt was recrystalized from hot water at 85° C. to yield 21 gm of potassium bitartarate, having purity >99%.

The filtrate obtained after removal of potassium bitartrate was mixed with 1.9 ltrs 90:10 acetone:water mixture and stirred for 45 min. The pectin precipitated was filtered and then washed first with 180 ml 50:50 acetone:water mixture, then with 200 ml 70:30 acetone:water mixture and finally with 200 ml acetone and then dried at 80° C. under vacuum to obtain dry pectin (yield 17 g). Pectin was further purified by washing it with acidified acetone:water mixture followed by washing with acetone:water mixture to remove excess acid and then drying.

The filtrate obtained after recovery of pectin was vacuum concentrated to recover acetone completely, and the filtrate was mixed with 7 g active charcoal, stirred for 25 min at 40° C. and filtered to remove activated charcoal. The carbon treatment was repeated. The filtrate was then vacuum concentrated at 70° C. to reduce the volume to 750 ml. The concentrate was then cooled to 7° C. and then 135 ml 20% aqueous potassium hydroxide solution added to it. The salt precipitated was recovered by filtration. The salt was washed with 3 aliquots of 50 water at 10° C. and washings added to the filtrate. The salt was recrystalized from hot water at 80° C. to yield 45 g potassium bitartarate having purity >99%.

The aqueous sugar solution containing other fruit acids was passed over a strong anion exchange macroporous resin in OH form having an exchange capacity 2 meq/ml. The solution was vacuum concentrated at 65° C. till the sugar content was 65%.

The other fruit acids on resin column were recovered by passing 1N hydrochloric acid thorough the column. This aqueous acid solution was concentrated and recrystalized to yield recrystalized fruit acids. The yield of fruit acids was 9 g.

Alternatively, the fruit acids on the resin column can also be recovered as their sodium salts by passing 1N NaOH through the column.

Example 7

500 gms of tamarind pulp was extracted for one hr with 1 ltr water at room temperature and filtered. The residue was extracted with fresh 1 ltr of water at room temperature. The procedure was repeated again six times. All filtrates were mixed together and 30 gms activated charcoal was added. The suspension was stirred for 15 min. at room temperature and filtered to remove activated charcoal. The filtrate was centrifuged to obtain a clear solution. This was vacuum concentrated at 60° C. to reduce the volume to 525 ml. The concentrate was then cooled to 10° C. and allowed to stand for 3 hrs. The salt precipitated was recovered by filtration. The salt was washed with 4 aliquots of 50 ml of water at 10° C. and washings added to the filtrate. The salt was recrystalized from hot water at 75° C. to yield 17 gm of potassium bitartarate having purity >99%.

The filtrate obtained after removal of potassium bitartarate was mixed with 1.4 ltrs of 90:10 methyl ethyl ketone/water mixture and stirred for 1 hr. The pectin precipitated was filtered and then washed first with 250 ml 85.15 methyl ethyl ketone:water mixture, then with 250 ml 95:5 methyl ethyl ketone:water and finally with 200 ml methyl ethyl ketone and then dried at 75° C. under vacuum to obtain dry pectin(yield 17 g). Pectin is further purified by washing it with acidified methyl ethyl ketone:water mixture followed by washing with methyl ethyl ketone:water mixture to remove excess acid and then drying.

The filtrate obtained after recovery of pectin was vacuum concentrated to recover methyl ethyl ketone completely and the filtrate was mixed with 10 g activated charcoal, stirred for 30 min at 75° C. and filtered to remove activated charcoal. The carbon treatment was repeated. The filtrate was then vacuum concentrated at 70° C. to reduce the volume to 550 ml. The concentrate was then cooled to 15° C. and then 165 ml 20% aqueous potassium hydroxide solution added to it. The salt precipitated was recovered by filtration. The salt was washed with 6 aliquots of 50 ml water at 5° C. and washings added to the filtrate. The salt was recrystalized from hot water at 75° C. to yield 52 g potassium bitartarate having purity >99%.

The aqueous sugar solution containing other fruit acids was passed over a strong anion exchange macroporous resin in OH form having an exchange capacity 1 meq/ml. The solution was vacuum concentrated at 65° C. till the sugar content was 65%.

The other fruit acids on resin column were recovered by passing 1N hydrochloric acid through the column. This aqueous acid solution was concentrated and recrystalized to yield recrystalized fruit acids. The yield of fruit acids was 10 g.

Alternatively the fruit acids on the resin column can also be recovered as their sodium salts by passing 1 N NaOH through the column. The main advantage of the present invention are:

1. It simplifies the process for recovery of potassium bitartarate, pectin, sugar, and fruit acids.
2. It eliminated the need for solvent extraction process and for recovery of solvent used in solvent extraction stage, thereby shortening the process time and lowering the equipment costs.
3. The process results in products of higher purity and better colour.
4. The process leads to higher yields.
5. The fruit acids are recovered as a separate product.

What is claimed is:

1. A process for the recovery of potassium bitartrate and pectin, sugars, fruit acids as by-products from tamarind pulp which comprises (i) extracting Tamarind pulp in 1–8 steps using 1:1 to 1:8 volumes of water, at a room temperature in the range of 25 to 100° C., by conventional method for about 0.5–6 hrs, to extract the mixture of tartaric acid, potassium bitartrate, pectin, sugar and other fruit acids in aqueous medium.

(ii) separating the residue and the supernatant with a conventional decolourising agent for a period of 0.5 to 2 hrs., separating the decolourising agent by conventional methods, to obtain clear liquid, concentrating the liquid separated, to reduce the volume to $\frac{1}{2}$ to $\frac{1}{10}^{th}$ of the original volume, at a temperature in the range of 60° C. to 90° C. under vacuum ranging between 20 mm and 80 mm to get a pulp, cooling the said concentrated pulp to 5 to 30° C. allowing it to stand for 2–16 hrs, to bring about complete separation of potassium bitartrate, and recovering from mother liquor potassium bitartrate by conventional methods, (iii) treating the mother liquor obtained in step (ii) containing small amount of potassium bitartrate, pectin, tartaric acid, sugar and the fruit acids with an organic solvent capable of precipitating pectin, washing the precipitate so formed by gradient washing with solvent:water mixture, further purifying pectin by treating it with acidified solvent:water mixture, (iv) removing the solvent from filtrate containing solvent, tartaric acid, traces of potassium bitartrate, sugar and other fruit acids, obtained in step (iii) completely, treating further the aqueous extract free from solvent with decolourising agent for a period ranging between 0.25 to 2 hrs, separating the decolourising agent by conventional methods, concentrating and cooling to a temperature in the range 30 to 5° C., further treating it with dilute aqueous alkali hydroxide solution for precipitation of additional potassium bitartrate, separating the supernatant and precipitate of potassium bitartrate by known methods, passing the supernatant from step (iv) rich in sugar, other fruit acids and containing small amount of potassium bitartrate over a conventional anion exchange resin to retain acids over the resin to separate sugar syrup which is concentrated to 60–70% sugar content, separating the sugar from the syrup by conventional methods and eluting the fruit acid adsorbed on the resin column by either a mineral acid or an alkali, recrystalizing to obtain the fruit acids, (v) pooling the precipitate of potassium bitartrate obtained in step (ii) and (iv) and purifying by known crystallization methods.

2. A process as claimed in claim 1, wherein the organic solvent used to treat the mother liquor for the precipitation of pectin is selected from alcohols or ketones or a mixture thereof in water.

3. A process as claimed in claim 1 wherein the alcohol used as solvent to treat the mother liquor is selected from the group consisting of methanol, ethanol, propanol, and isopropanol.

4. A process as claimed in claim 1 wherein the ketone used as a solvent to treat the mother liquor is selected from the group consisting of acetone, methyl ethyl ketone and methyl isobutyl ketone.

5. A process as claimed in claim 1 wherein the acid used to acidify the solvent:water mixture is a mineral acid selected from the group consisting of hydrochloric acid, sulphuric acid and nitric acid.

6. A process as claimed in claim 1 wherein the preferred acid used to acidify the solvent:water mixture is hydrochloric acid.

7. A process as claimed in claim 1 wherein the anion exchange resin is selected from a family of either gel type or macroporous strong, weak or medium basic anion exchange resin having a capacity in the range 0.2–3 meq/ml.

8. A process as claimed in claim 1 wherein the preferred capacity of the anion exchange resin is in the range of 0.5–2.5 meq/ml.

9. A process as claimed in claim 1 wherein the most preferred capacity of the anion exchange resin is in the range of 1–2 meq/ml.

10. A process as claimed in claim 1 wherein the decolourising agent is selected from activated carbon, fuller's earth, or kiesselguhr.

11. A process as claimed in claim 1 wherein the preferred decolourising agent is activated carbon.

* * * * *